United States Patent
Driscoll

(10) Patent No.: US 9,861,605 B2
(45) Date of Patent: Jan. 9, 2018

(54) ENRICHED INJECTABLE EMULSION CONTAINING SELECTED FATTY ACID TRIGLYCERIDES

(71) Applicant: STABLE SOLUTIONS LLC, Goleta, CA (US)

(72) Inventor: David F. Driscoll, Bridgewater, MA (US)

(73) Assignee: STABLE SOLUTIONS LLC, Goleta, CA (US)

( * ) Notice: Subject to any disclaimer, the term of this patent is extended or adjusted under 35 U.S.C. 154(b) by 49 days.

(21) Appl. No.: 14/354,010

(22) PCT Filed: Oct. 24, 2012

(86) PCT No.: PCT/US2012/061624
§ 371 (c)(1),
(2) Date: Apr. 24, 2014

(87) PCT Pub. No.: WO2013/063067
PCT Pub. Date: May 2, 2013

(65) Prior Publication Data
US 2014/0316001 A1    Oct. 23, 2014

Related U.S. Application Data

(60) Provisional application No. 61/550,659, filed on Oct. 24, 2011.

(51) Int. Cl.
| | |
|---|---|
| *A61K 31/225* | (2006.01) |
| *A61K 31/232* | (2006.01) |
| *A61K 9/107* | (2006.01) |
| *A61K 9/00* | (2006.01) |
| *A61K 31/231* | (2006.01) |

(52) U.S. Cl.
CPC .......... *A61K 31/232* (2013.01); *A61K 9/0019* (2013.01); *A61K 9/107* (2013.01); *A61K 31/231* (2013.01)

(58) Field of Classification Search
None
See application file for complete search history.

(56) References Cited

U.S. PATENT DOCUMENTS

| | | | |
|---|---|---|---|
| 4,526,793 A | | 7/1985 | Ingenbleek et al. |
| 2010/0069686 A1 | | 3/2010 | Waibel et al. |
| 2010/0080762 A1 | | 4/2010 | Goralczyk |
| 2011/0206741 A1 | * | 8/2011 | Lee et al. ............... 424/400 |

FOREIGN PATENT DOCUMENTS

| | | |
|---|---|---|
| AU | 617570 | 7/1990 |
| EP | 0 376 852 B1 | 7/1990 |
| WO | WO 1991016443 A1 * | 10/1991 |
| WO | WO 2004064716 A2 * | 8/2004 ............ A61K 31/20 |

OTHER PUBLICATIONS

Hamazaki et al. Lipids 22 (1987) 1031-1035 published in 1987.*
Yamashita et al. Clinical Immunology and Immunopathology, 1991 (59) Abstract.*
Nakamura et al. Journal of Clinical Investigation, 1993 (92) 1253-1261.*
International Search Report issued in corresponding International Application No. PCT/US2012/061624, dated Jan. 7, 2013.
Bach, A.C. et al., "Clinical and Experimental Effects of Medium-Chain•Triglyceride-Based Fat Emulsion—A Review", Clinical Nutrition, 8:223-35. (1989) (abstract only).
Calder, P.C. et al., "The 2008 ESPEN Sir David Cuthbertson Lecture: Fatty Acids and Inflammation—From the Membrane to the Nucleus and From the Laboratory Bench to the Clinic", Clinical Nutrition, vol. 29, pp. 5-12 (2010).
Driscoll, D.F. et al., Phenytoin Toxicity in a Critically Ill, Hypoalbuminemic Patient With Normal Serum Drug Concentrations, Grit Care Med, vol. 16, No. 12, pp. 1248-1249 (1988).
Driscoll, D.F. et al., "The Influence of Medium•Chain Triglycerides on the stability of All-in-One Formulations", International Journal of Pharmaceutics, vol. 240, pp. 1-10 (2002).
Driscoll, D.F., "Lipid Injectable Emulsions: Pharmacopeial and Safety Issues", Pharmaceutical Research, vol. 23, No. 9, pp. 1959-1969 (Sep. 2006).
Driscoll, D.F. et al., "Parenteral and Enteral Nutrition in the Intensive Care Unit", Intensive Care Medicine, Wolters Kluwer Lippincott Williams & Wilkins, pp. 1974-1990 (2012).
Driscoll, D.F. et al., "Pharmacopeial Compliance of Fish Oil—Containing Parenteral Lipid Emulsion Mixtures: Globule Dize Distribution (GSD) and Fatty Acid Analyses", International Journal of Pharmaceutics, vol. 379, No. 1, pp. 125-130 (2009).
Fish Oil, Rich in Omega-3 Fatty Acid. Monograph No. 1912, European Pharmacopeia, 6.0, pp. 1893-1895. (2008).
Harris, W.S., "The Omega-3 Index: Clinical Utility for Therapeutic Intervention", Curr Cardiol Rep, vol. 12, pp. 503-508 (2010).
Lee J.S. et al., "Saturated, But Not n-6 Polynsaturated, Fatty Acids Induce Insulin Resistance: Role of Accumulation of Lipid Metabolites", J. Appl. Physiol, vol. 100, pp. 1467-1474 (2006).

(Continued)

*Primary Examiner* — Jeffrey S Lundgren
*Assistant Examiner* — Michael Schmitt
(74) *Attorney, Agent, or Firm* — Buchanan Ingersoll & Rooney PC

(57) ABSTRACT

A composition including a triglyceride containing glycerol which is esterified with three fatty acids, wherein the three fatty acids include at least one fatty acid selected from caprylic acid, capric acid, α-linolenic acid, linoleic acid, oleic acid, arachidonic acid, eicosapentaenoic acid, docosahexaenoic acid and docosapentaenoic acid. The total amount of caprylic acid, capric acid, a-linolenic acid, linoleic acid, oleic acid, arachidonic acid, eicosapentaenoic acid, docosahexaenoic acid and docosapentaenoic acid is greater than 60%, based on the total weight of the fatty acids in a base or starting emulsion. The various physical mixtures of triglycerides containing the primary therapeutic fatty acid can be blended to form pre-defined amounts for the treatment of various acute pathological conditions.

17 Claims, No Drawings

(56) References Cited

OTHER PUBLICATIONS

Lovaza™ (omega-3 acid ethyl esters) Capsules. Package insert. Reliant Pharmaceuticals, Inc., Liberty Corner, NJ, USA (Jun. 2007).

Lowell, J.A. et al., "Postoperative Fluid Overload: Not a Benign Problem", Crit Care Med, vol. 18, pp. 728-733 (Jul. 1990) (abstract only).

Maalouf, M.A. et al., "The Neuroprotective Properties of Calorie Restriction, The Ketogenic Diet, and Ketone Bodies", Brain Res. Rev., vol. 59, No. 2, pp. 293-315 (2009).

Omega-3 Acid Triglycerides, European Pharmacopeia, (believed to correspond to pp. 2554 2556). (2008).

Rangel-Fausto, M.S. et al., "The Natural History of Systemic Inflammatory Response Syndrome (SIRS): A Prospective Study", JAMA, vol. 273, No. 2, pp. 117-123 (1995).

Senior Jr. "Medium Chain Triglycerides" University of Pennsylvania Press, Philadelphia, 1968.

Serhan, C.N. et al., "Resolving Inflammation: Dual Anti•Inflammatory and Pro-Resolution Lipid Mediators", Nature Reviews, vol. 8, pp. 349-361 (2008).

Simopoulos, A., "Evolutionary Aspects of Dietary Omega-3 Fatty Acid Ratio: Medical Implications", World Rev Nutr Diet 2009;100:1-21.

Wanten GJA, Calder PC. Immune modulation by parenteral lipid emulsions. Am J Clin Nutr 2007;85:1171-84.

Notification Concerning Transmittal of International Preliminary Report on Patentability (Chapter I of the Patent Cooperation Treaty)(Form PCT/IB/326 & Form PCT/IB/373) and the Written Opinion of the International Searching Authority (Form PCT/ISA/237) dated May 8, 2014, in the corresponding International Application No. PCT/US2012/061624. (8 pages).

\* cited by examiner

ENRICHED INJECTABLE EMULSION CONTAINING SELECTED FATTY ACID TRIGLYCERIDES

RELATED APPLICATION

This application claims the benefit of priority of U.S. Provisional Application No. 61/550,659 filed on Oct. 24, 2011, the entire contents of which are hereby incorporated by reference in their entireties.

FIELD

Disclosed is a composition comprising at least one triglyceride containing glycerol which is esterified with three fatty acids. Also disclosed is a method of parenterally administering a composition to treat a predetermined condition. Further disclosed is a system for formulating a composition for parenteral administration, and a method of determining an effective formulation for treating a predetermined condition.

BACKGROUND INFORMATION

Due to the inherent water-insolubility of long-chain hydrocarbons, the parenteral provision of long-chain fatty acids such as the omega-3 fatty acids (e.g., the 18-carbon alpha linolenic acid, or ALA; the 20-carbon eicosapentaenoic acid, or EPA, and the 22-carbon docosahexaenoic acid, or DHA, and the 22-carbon docosapentaenoic acid, or DPA), and the omega-6 fatty acids (e.g., the 18-carbon linoleic acid, or LA, and the 20-carbon arachidonic acid, or AA), and the omega-9 fatty acid (e.g., the 18-carbon oleic acid, or OA), can require a triglyceride-based, oil-in-water emulsion delivery system for safe administration by the intravenous route of administration. A similar problem relating to water-insolubility is also encountered with medium-chain fatty acids (i.e., caprylic acid, capric acid), a common issue with hydrocarbons. Although some of these fatty acids are available as ethyl esters, there is no clinical experience demonstrating their safety upon intravenous infusion, and there are significant stability and toxicity concerns when they are prepared as sterile lipid injectable emulsion dosage forms.

To illustrate the stability challenges of injectable emulsion formulations as they relate to solubility or miscibility as homogenous dispersions, there is, for example, an approximate 100-fold difference in the aqueous solubility of the 8-carbon saturated fatty acid (FA), caprylic acid (0.7 g/L), compared to the 16-carbon saturated fatty acid FA, palmitic acid (0.007 g/L). Thus, not surprisingly, aqueous solubility worsens with increasing numbers of carbon atoms. The insolubility or immiscibility between two liquids (e.g., oil and water) gives rise to competing adhesive forces, or tension, between the liquids at their interface, keeping the liquid phases separate from one another. Miscibility of the two liquids can be determined by measuring the interfacial tension that exists between them, and the less miscible they are, the higher the tension at these liquid interfaces. As an example, the interfacial tension between caprylic acid, an 8-carbon compound, and water, is approximately 8.2 dyne/cm, whereas for the 18-carbon oleic acid against water it is nearly twice as high at 15.6 dyne/cm. Thus, triglyceride-based, oil-in-water emulsions are the only established vehicles for safely providing adequate amounts of non-polar, medium- and long-chain FAs intravenously, since it can be desirable for all such infusions to be miscible with blood upon injection, given its polar (water-soluble) characteristics. Moreover, as triglycerides, the clinical toxicology concern regarding the metabolic rate of formation of parenteral free FAs in the blood stream upon metabolism, thus producing systemic toxicity, is mitigated, as compared to the faster rate of release from lower molecular weight ethyl esters. Hence, the triglyceride oil is in the dispersed or internal phase and water is in the continuous or external phase. In contrast, water-in-oil emulsions cannot be given intravenously, as the oil phase is now in the external phase, which dictates the physical properties of the emulsion, and hence such emulsions would be immiscible with blood. This could lead to a potentially fatal intravascular embolism.

Parenteral oil-in-water emulsions also allow water-insoluble drugs and/or nutrients to be incorporated into the dispersed, or internal, oil phase that is distributed throughout the continuous, or external, aqueous phase. These two phases are made miscible by lowering the interfacial tension between oil and water by using an amphoteric emulsifying agent, such as egg phospholipids. Several injectable nutritional and drug emulsions are widely used in this manner in the clinical setting. Once formulated, it is imperative for the intravenous emulsions to remain physically stable, i.e., homogeneously dispersed submicron oil droplets in the continuous aqueous phase—otherwise separation of the oil phase from the water phase may lead to embolization from the formation of coalesced, large-diameter (>5 µm) fat globules in the microvasculature. This may result in increased risk of morbidity (e.g., capillary embolism, cellular damage from oxidative stress, and accumulation of fat in the liver and accompanying hepatic dysfunction evidenced by elevated liver enzymes) and possibly, mortality. In the physiologically compromised critically ill, the risk of harm from an unstable intravenous emulsion is greatly heightened in this setting.

Direct infusion of FAs into the bloodstream is potentially dangerous, and the free FA concentration in current lipid injectable emulsions for infusion is limited (Driscoll, 2006). All injectable oil-in-water emulsions containing medium-chain FAs (e.g., caprylic acid) and long-chain FAs (e.g., LA, EPA and DHA, etc.) for clinical use are derived from plant or marine oil triglycerides. Each triglyceride source has a distinctive FA profile with some oils containing high amounts of certain FAs, such as: a) linoleic acid (i.e., soybean oil, ≥50%), b) caprylic acid (MCT oil, ≥70%), c) oleic acid (i.e., olive oil, ≥80%). But for sources of fish oil triglycerides, there is a unique and significant pharmaceutical issue relating to quality (i.e., concentrations of the omega-3 FAs, EPA and DHA), which may have clinical implications given their potential therapeutic use to treat various diseases. Official pharmacopeias, which set the standards for drug purity and safety in various countries, have provided separate drug monographs for the concentrations of EPA and DHA in fish oil triglycerides. For example, the European Pharmacopeia (EP) wrote the first monograph (EP 1352) in 1999 ("Omega-3 Acid Triglycerides"). In it, the concentrations of the two principal bioactive omega-3 FAs, EPA and DHA, expressed as triglycerides, are specified to have a minimum sum concentration of 45 percent, and further, that the total of all omega-3 FAs have a minimum concentration of 60 percent. Six years later in 2005, EP 1912 was adopted ("Fish Oil, Rich in Omega-3 Acids"). In this monograph, the minimum concentration of EPA and DHA, also expressed as triglycerides, is required to be 22 percent (with a specified minimum EPA content of 13 percent, and a DHA concentration of 9 percent), and the total of all omega-3 FAs must have a minimum concentration of 28 percent. Hence, two active pharmacopeial monographs exist with EP 1912 requiring only approximately one-half the minimum concentration of omega-3 fatty acids as that stipulated in the original EP 1352 monograph.

During a laboratory investigation of commercially available products, a comparison of the FAs profile of two formulations revealed that although one formulation contained approximately 50% higher concentrations of total fish oil triglycerides than the other formulation (i.e., 15% vs. 10%), it contained approximately 50% lower concentrations of the certain bioactive omega-3 fatty acids, EPA and DHA (Driscoll et al, 2009). Consequently, the product with the lower EPA and DHA concentrations had higher amounts of other long-chain saturated FAs (e.g., myristic, palmitic and stearic acids). Although the formulations are routinely used for acutely ill patients, the FAs profiles are not therapeutically equivalent. Thus, two European manufacturers opted to apply separate EP monographs for their commercial omega-3 FA-containing injectable emulsion products. The discrepancy between these emulsion formulations continues today. Since there is a potentially clinically significant pharmacological/therapeutic role of fish oil (vis-à-vis the EPA and DHA concentrations therein), well beyond its nutritional indications, the different omega-3 FA contents of the different fish oil triglyceride sources included in these products can require careful calculation to ensure that therapeutically effective dosages of omega-3 FAs are prescribed for the desired clinical effects. When they are prescribed as a therapeutic (vs. nutritional) agent, a case can be made that for intravenous administration, it can be beneficial to use the purest (most concentrated) form of omega-3 FAs-containing oil in injectable emulsions, especially for critically ill patients. This may be particularly true for all current sources (plant or marine) of parenteral triglycerides since they all contain several unnecessary and/or undesirable FAs. For example, the 16-carbon saturated FA, palmitic acid, is present in soybean oil, olive oil and fish oil in concentrations approximating 10% of the total FAs profile. Excessive amounts of long-chain saturated FAs ($\geq 14$ carbons), such as palmitic acid in the diet (or present in the less refined emulsions), for example, can be pro-inflammatory, and can interfere with glucose uptake by skeletal muscle (Lee et al, 2006). In critically ill patients, glucose intolerance (i.e., hyperglycemia) is a clinically significant risk factor for increased morbidity and mortality (Driscoll and Bistrian, 2012). Hence, seeking a highly purified and enriched source of selected FAs (as MCTs and LCTs) for parenteral administration is desirable.

In the various plant and fish oils included in current lipid injectable emulsion products, more than 15 different FAs, containing from 6 to 22 carbons (Wanten and Calder, 2007), are present on a triglyceride or triacylglycerol backbone at positions sn-1, sn-2 or sn-3. These include both saturated (no double bonds) and unsaturated (one or more double bonds) FAs, and the greater the number of double bonds present, the greater the risk of oxidative degradation. Fatty acids are described using a specific nomenclature involving three general terms: 1) the number of carbon atoms; 2) the number of double bonds; and, 3) the carbon atom containing the first double bond. The source of FAs (plant or marine) determines the final FA profile. For example, processed coconut oil used to make MCT oil is a rich source of saturated medium-chain FAs, caprylic acid (~75%) and capric acid (~25%). Processed soybean oil is a rich source of unsaturated FAs, including omega-6 FAs (linoleic acid, ~50%), omega-9 FAs (oleic acid, 25%), and omega-3 fatty acids, (alpha linolenic acid, ~10%). Processed fish oil is rich in omega-3 FAs (sum of EPA and DHA, $\geq 22\%$ to $\geq 45\%$).

The medium-chain, saturated FAs contain no double bonds, come from plant sources such as coconut oil, and are present as medium chain triglycerides (MCTs). They primarily include the 8-carbon caprylic acid (~75%), denoted simply as 8:0, and the 10-carbon capric acid (~23%), denoted as 10:0 (Senior, 1968). Currently, there are no commercial lipid injectable emulsions made exclusively from MCTs, but rather MCTs are present in various products in a mixture with other oils such as soybean, and/or olive and fish oils. Initial concerns of clinically significant ketogenesis arising from the metabolism of MCTs were not realized based on its vast clinical experience with them over the last 25 years when given in daily doses of 50 to 100 g per day as a parenteral nutrition supplement. In these cases MCTs were prescribed as a dense calorie source, and when given with hypertonic glucose as part of a parenteral nutrition support regimen, the resulting hyperinsulinemic response upon infusion mitigates ketogenesis (Bach et al., 1989). With lower insulin levels, however, a modest ketogenesis is observed, which can be therapeutically desirable in certain patients. For example, ketogenic diets have been suggested for certain patients refractory to neuroleptic therapy for seizures, as well as for neuroprotection in various neurological diseases (Maalouf et al, 2009), which may include traumatic brain injury of varying origin.

Omega-3, -6, and -9 FAs are classified as unsaturated fatty acids, containing one or more double bonds. The three main families of unsaturated FAs important in human metabolism include 1) the omega-3's, e.g., alpha-linolenic acid, or ALA, containing 18 carbons and 2 double bonds beginning on the $3^{rd}$ carbon (hence, "omega-3" or "n3") from the methyl end of the hydrocarbon chain, denoted as 18:2n3; eicosapentaenoic acid, or EPA, containing 20 carbons and 5 double bonds beginning on the $3^{rd}$ carbon, denoted as 20:5n3; and, docosahexaenoic acid, or DHA, containing 22 carbons and 6 double bonds beginning on the $3^{rd}$ carbon, denoted as 22:6n3; and, docosapentaenoic acid, or DPA, containing 22 carbons and 5 double bonds beginning on the $3^{rd}$ carbon, denoted as 22:5n3; 2) the omega-6's, e.g., arachidonic acid, or AA, containing 20 carbons and 4 double bonds beginning on the $6^{th}$ carbon (hence, "omega-6" or "n6"), denoted as 20:4n6 and linoleic acid, or LA, containing 18 carbons and 2 double bonds beginning on the $6^{th}$ carbon, denoted as 18:2n6; and finally, 3) the omega-9's (e.g., oleic acid containing 18 carbons and 1 double bond beginning on the $9^{th}$ carbon (hence, "omega-9" or "n9"), denoted as 18:1n9. The omega-3 and omega-6 FAs are classified as polyunsaturated (more than one double bond), while the omega-9 FAs are monounsaturated.

In human metabolism, Western diets are disproportionately high in omega-6 FAs (Simopoulos, 2009). Because the cell membranes are composed of lipids, they are a reflection of recent dietary intake of various fats. Moreover, all cells have a finite lifespan in the circulation, such as, for example: approximately 120 days for red blood cells; approximately 10 days for platelets; and approximately 6 hours for white blood cells. In the case of white blood cells, once they are released from the bone marrow or lymphoid tissues, the short time in the circulation reflects the fact that they are merely being transported to local tissues in response to an immunogenic stimulus. But once at the site of injury, they may survive for as long as a few days during phagocytosis. Thus, cells of the body are constantly turning over with dietary intake of fats being continually used to construct plasma cell membranes during the process of hematopoiesis. In addition, there is a more rapid interchange of FAs in cell membranes of circulating cells. The dietary sources of FAs in human metabolism are important because the body produces endogenous chemical mediators derived from these membrane-bound lipids. This would include, for example, the eicosanoids and leukotrienes, which have a profound effect on the body's metabolic response to injury. The bioactive mediators produced from omega-6 fatty acids include specific eicosanoids, which have more pro-inflammatory/pro-coagulable properties deriving from the "2-series" of prostglandins and thromboxanes, which are highly vasoactive. As well, production of leukotrienes of the "4-series", also from dietary omega-6 FAs in cell membranes, heightens the immune response, increases oxidative stress, and promotes inflammation. Therefore, in this case, altering the sources of daily intakes of dietary lipids, with an emphasis on increasing the absolute intakes of omega-3 FAs, causes a metabolic shift to the "3-series" eicosanoids and "5-series" leukotrienes, which are less vasoactive, and therefore less inflammatory and immunogenic. Consequently, facilitating these changes at the cellular level by the pharmacological dosing of precise amounts of parenterally administered selected FAs (in this case, omega-3's) may ultimately be associated with improvements in morbidity and mortality in a number of clinical conditions involving acute and severe catabolic stress. Furthermore, there are resolvins made from EPA and DHA, as well as neuroprotectins made from DHA that have active anti-inflammatory roles to resolve inflammation. Lipoxins from AA can, under certain circumstances, play a similar role. For example, incorporation of omega-3 FAs into cell membranes, and thus significantly altering eicosanoid metabolism with potential therapeutic implications, is best measured in red blood cells (RBCs). They have a long lifespan, exhibit the lowest biological variability, and the omega-3 FAs concentrations in RBC membranes is not altered by the "fed state". From these observations, the "Omega-3 Index", which is expressed as the sum of EPA and DHA as a percentage of total identified RBC FAs, is useful, with a defined range of 4% to 8% having therapeutic implications (Harris, 2010). For instance, risk of major cardiac events is increased when EPA and DHA levels fall below 4%, whereas cardioprotection was observed when levels were above 8%.

In the critically ill, there are numerous ongoing metabolic insults from various sources. For example, certain patient populations, such as those with head trauma, $3^{rd}$ degree burns, long-bone fractures and culture-confirmed blood infections (sepsis), have a very high level of metabolic stress, as evidenced by, for example, standard severity-of-illness scoring systems (e.g., Acute Physiology and Chronic Health Evaluation, or APACHE II, Simplified Acute Physiology Score or SAPS II, and the Injury Severity Score, or ISS). The scoring criteria include various patient factors upon admission to the intensive care unit (ICU), e.g., vital signs and certain blood values, but in all such cases of severe metabolic stress, patients universally have general inflammation, otherwise known as the Systemic Inflammatory Response Syndrome (SIRS), an indicator of the intensity of the metabolic response during critical illness, along with elevated blood levels of C-reactive protein. During this time, such patients are highly catabolic, i.e., have pronounced loss of protein from skeletal muscle to support the metabolic response to injury (e.g., protein breakdown to provide gluconeogenic amino acids to meet heightened energy needs). Hence, the loss of lean tissue (skeletal muscle proteolysis), which represents the metabolically active body cell mass, is a major component of the body's response to injury and/or infection, and ultimately, a crucial component in the recovery from critical illness. In the well-nourished patient, such losses can be tolerated for longer periods without nutrition support intervention (parenteral and/or enteral), compared to the patient who is moderately to severely malnourished. Lean tissue losses can be estimated from a measurement of urea nitrogen from a 24-hour urine collection. Every 1 gram of nitrogen lost represents approximately 30 g of lean tissue. Thus, critically ill patients with a 24-hour nitrogen loss of ≥15 g/day (approximately equal to one pound of hydrated lean tissue daily) would be considered to be in severe catabolic stress. Not surprisingly, in the case of pre-existing malnutrition now accompanied by critical illness, the time for intervention before significant clinical complications occur is substantially shorter and can require immediate metabolic attention. Judicial provision of parenteral and/or enteral nutrition support (i.e., permissive underfeeding) is often instituted during this time, and begins to offset the extraordinary protein losses, but it is of reduced efficacy and/or benefit until the underlying stress response remits (Driscoll and Bistrian, 2012).

During this period of severe metabolic stress, the function of vital organs (e.g., brain, heart, lungs, liver and kidneys) may be compromised, and this is especially true if organ impairment is present prior to admission to the ICU. For example, patients may be at increased risk because of longstanding diseases such as asthma, chronic obstructive pulmonary disease (COPD), chronic renal failure (CRF), congestive heart failure (CHF) or end-stage liver disease (ESLD). Moreover, the clinical situation may be acutely worsened in the ICU because of iatrogenesis. That is, during treatment of the critically ill, certain medical interventions may worsen organ function. For example, acute fluid overload from large-volume intravenous fluids administered for intravascular resuscitation and to maintain hemodynamic stability may cause clinically significant changes in serum electrolytes and acid-base balance affecting cardiac function, which may increase the need for mechanical ventilatory assistance, and may worsen kidney function. Thus, compromised or failing vital organs (i.e., acutely, chronically or both) accentuates the metabolically stressed state and likely increases medical complications affecting clinical outcome.

Finally, the pharmacokinetics and pharmacodynamics of the various drugs commonly prescribed to critically ill patients are also affected during severe metabolic stress. Clearly, the disposition of the drugs throughout the body and delivery to their target site(s) of action (i.e., pharmacokinetics), will be altered. That is, changes in blood flow will greatly influence the successful delivery of sufficient concentrations of drug to its site of action in order to exert its therapeutic effects (i.e., pharmacodynamics). Alterations in the circulatory system may occur as part of the physiologic response to active stress. For example, in a hemodynamically unstable state, the body re-directs blood flow from the splanchnic circulation and skin to support vital organs and functions; during adult respiratory distress syndrome (ARDS), hypoxic vasoconstriction occurs to avoid attempts by the body to ventilate poorly perfused segments of the lung; and, serum albumin precipitously falls during acute metabolic stress and inflammation, thus altering drugs that are highly plasma protein bound, which may increase the toxicity of drugs which have a narrow therapeutic index (Driscoll et al, 1988). These and other adaptive physiologic responses to severe metabolic stress are consequential to outcome, and may also affect the safety and efficacy of drug therapies during critical illness, which may be amenable to selected FAs therapies via specially-processed triglycerides from exemplary lipid injectable emulsion formulations in specific amounts and/or combinations.

Some reduction in the severely stressed metabolic state may be achieved by specifically-targeted medical interventions (e.g., optimized antimicrobial therapy for culture-confirmed microorganisms, aggressive diuresis and vasopressor infusions) and selected surgical interventions (e.g., excision of necrotic tissues, repair of major blood vessels and surgical drainage of abscesses). But in these circumstances, like nutrition support intervention above, the efficacy of such clinical maneuvers may be self-limiting and take several days to begin the healing processes. During this period of convalescence, the metabolic milieu maintains a "net" inflammatory state, which eventually wanes over time. It would be desirable to hasten the resolution time of the net inflammatory state, and subsequent healing process(es), therefore improving outcomes in the ICU.

Omega-3 FAs, and in particular EPA and DHA, have been subject to intense investigation as potential therapeutic agents in diseases associated with inflammation, oxidative stress, ischemia and immune function. The emerging cellular and molecular mechanisms that underlie the therapeutic effects of omega-3 FAs have been reviewed (Serhan et al, 2008). A recent review of the potentially wide-ranging clinical indications for these exemplary FAs has been published, showing that by increasing the supply of omega-3 FAs to alter the FA composition of cell membranes, there are profound downstream effects on the cellular response to metabolic stress (Calder, 2010). For example, the systemic anti-inflammatory properties of omega-3 fatty acids, via modulation of eicosanoid precursors (prostaglandins and thromboxanes) of the "2-series" to the less vasoactive "3-series" in cell membranes, can be dosed to treat a number of acute diseases of inflammation (e.g., systemic inflammatory response syndrome marked by elevated C-reactive protein levels in the critically ill) as well as chronic diseases of inflammation (e.g., rheumatoid arthritis). This metabolic modulation reduces the intensity of a prolonged and often over-exuberant, omega-6 FA-induced inflammatory response, which has pathological implications. In addition, the immune response is also favorably modified by omega-3 FAs supplementation by altering recruitment of neutrophils for phagocytosis by similar modulation of other important endogenous mediators, i.e., leukotrienes, from the relative hyperimmune "4-series" to the less immunogenic "5-series". This, in turn, can favorably modify the intensity of the immune response, and reduce the accompanying oxidative stress from the production of reactive oxygen species during phagocytosis. Because of the metabolically important and common interplay of the physiological responses involved (inflammation, oxidative stress, ischemia and immune function), and the metabolic stresses from various etiologies (e.g., infection, trauma, burns, compromised vital organ functions, etc.), the safe parenteral provision and effective uptake of omega-3 FAs may have a clinically significant effect on therapeutic outcome. This may be particularly true when such provision is accompanied by effectively applied standard treatment regimens (e.g., antibiotics, hemodynamic stability, fluid, electrolyte and acid-base management, surgical repair, etc.).

Conventional, high molecular weight sources of omega-3 FAs, such as fish oil triglycerides, can contain various (10-15) saturated and unsaturated FAs that are found on the triglyceride backbone at positions sn-1, sn-2 or sn-3 as found in nature. Of these FAs present, less than half are of therapeutic importance. A more purified FA profile that contains a specific amount of a therapeutic FA or combination thereof, and thus is devoid of undesirable, and possibly deleterious FAs, is therefore desirable. For example, as described above regarding the two official monographs, EP 1352 and EP 1912, the omega-3 FAs fraction is only between 30 and 60% (respectively), whereas the remaining FAs comprise from between 40% and 70% (approximately). In contrast, and at present, an oral capsule dosage form of EPA and DHA provided as ethyl esters exists as an FDA-approved product "Lovaza™" indicated, "as an adjunct to diet to reduce triglyceride (TG) levels in adult patients with very high (≥500 mg/dL) triglyceride levels". This occurs presumably by reducing "the synthesis of triglycerides (TGs) in the liver because EPA and DHA are poor substrates for the enzymes responsible for TG synthesis, and EPA and DHA inhibit esterification of other fatty acids" (Lovaza, 2007). Further, it states: "Each one gram capsule of Lovaza (omega-3-acid ethyl esters) contains at least 900 mg of the ethyl esters of omega-3 fatty acids. These are predominantly a combination of ethyl esters of eicosapentaenoic acid (EPA—approximately 465 mg) and docosahexaenoic acid (DHA—approximately 375 mg)". Thus, compared to the highest minimum limits for EPA and DHA of the European Pharmacopeia (i.e., EP 1352) of 45%, the concentrations of EPA and DHA in Lovaza™ are at least twice as high as the concentrations contained in current sources of fish oils that are approved for clinical use, and therefore they are of far greater purity. Application of an exemplary, highly purified selected FA or mixture of FAs, as parenteral triglycerides, may lead to a safer source, and more precise dosing of therapeutic FAs to target therapies for specific clinical conditions than presently available options. Moreover, given the higher purity of selected FAs, parenteral oil-in-water formulations containing various combinations of desirable FAs from purified triglyceride mixtures can be devised for parenteral administration in far smaller volumes than is possible using less purified sources or natural oil sources, which addresses another major clinical issue in critically ill, fluid overloaded patients (Lowell et al, 1990).

In other cases of acute illness, certain FAs may also be beneficial. During myocardial infarction, provision of omega-3 FAs may reduce ischemia in the coronary vessels. Severe hepatic steatosis that compromises liver function may be treated with omega-3 FAs. For example, patients with epileptic seizures that are refractory to anticonvulsant therapy may uniquely respond to the provision of medium-chain fatty acids that produce a mild, but therapeutic, ketogenesis. Thus, medical emergency situations that can require immediate intervention may also be amenable to targeted FAs therapy. Moreover, the neuroprotective effects of medium-chain FAs may be beneficial in traumatic brain injury, and potentially synergistic by the concomitant intravenous administration of omega-3 FAs.

At present, there are three general forms of triglycerides available for parenteral use as lipid injectable emulsions: 1) natural sources containing an array of various FAs (e.g., coconut oil with approximately 80% of the FAs profile containing 6 to 14 carbons, with approximately 10 to 13% as the medium chain FAs, caprylic acid and capric acid, in nearly equivalent amounts); 2) "processed" natural sources containing selected FAs (e.g., coconut oil that has undergone steam hydrolysis and double distillation, principally yielding caprylic and capric acid and comprising >95% of FAs that are re-esterified to glycerol forming "MCT Oil"); 3) structured triglycerides made from natural sources that are hydrolyzed to yield a unique FA profile (e.g., re-transesterification after random mixing of the selected FAs, yielding unique triglycerides that contain various amounts of each FA, depending on the starting proportions of each oil such as the former product known as Structolipid™ containing 64% soybean oil and 36% MCT oil (by weight).

In many clinical conditions, certain FAs may have therapeutic benefits, but may require highly specific doses of the selected FA(s). Of the three above options, there is no way to precisely deliver selected FAs for the intended parenteral FA therapy in a particular clinical condition. Thus, in all cases, either undesirable FAs or less precise FA concentrations severely compromise the clinical testing of FAs as pharmacological therapy for many acute disease conditions.

SUMMARY

According to an exemplary aspect, disclosed is a composition comprising at least one triglyceride containing glycerol (1,2,3-propanetriol) which is esterified with three FAs, hence a triacylglycerol, which is esterified with three FAs, hence a triacylglycerol, wherein the three FAs are the same as each other, wherein each of the three FAs that are the same as each other is caprylic acid, capric acid, α-linolenic acid, linoleic acid, oleic acid, arachidonic acid, eicosapentaenoic acid, docosahexaenoic acid or docosapentaenoic acid, and wherein a total amount of caprylic acid, capric acid, α-linolenic acid, linoleic acid, oleic acid, arachidonic acid, eicosapentaenoic acid, docosahexaenoic acid or docosapentaenoic acid is greater than 60%, based on the total weight of the FAs present.

According to an exemplary aspect, disclosed is a method of parenterally administering a composition to treat a predetermined condition, the method comprising: parenterally administering an exemplary composition to a person having the predetermined condition.

According to an exemplary aspect, disclosed is a composition comprising at least one triglyceride containing glycerol which is esterified with three FAs, wherein the three FAs are the same as each other, wherein each of the three FAs that are the same as each other is caprylic acid, capric acid, α-linolenic acid, linoleic acid, oleic acid, arachidonic acid, eicosapentaenoic acid, docosahexaenoic acid or docosapentaenoic acid, and wherein a content of the FAs present in the at least one triglyceride containing glycerol which is esterified with three FAs that are the same as each other, is greater than 60%, based on a total weight of FAs of the composition.

According to an exemplary aspect, disclosed is a system for formulating a composition for parenteral administration, the system comprising at least a first composition and a second composition, wherein the first and second compositions are separately contained from each other, wherein each composition contains at least one triglyceride containing a glycerol which is esterified with three FAs that are the same as each other, wherein a content of the FAs present in the at least one triglyceride is greater than 60%, based on a total weight of FAs of the first composition, wherein the three FAs of the triglyceride of the first composition are different from the three FAs of the triglyceride of the second composition.

According to an exemplary aspect, disclosed is a method of formulating a composition, the method comprising: providing an exemplary system; and mixing at least two of the separately contained compositions.

According to an exemplary aspect, disclosed is a method of determining an effective formulation for treating a predetermined condition, the method comprising: providing an exemplary system; mixing at least two of the separately contained compositions to produce a plurality of distinct samples; and testing at least one of the distinct samples to determine whether the tested distinct sample is effective to treat the predetermined condition.

DETAILED DESCRIPTION

Alterations in fatty acid status and metabolism can play a role in clinical outcome of various diseases. The use of polyunsaturated, long-chain omega-3 fatty acids during acute inflammation can be observed, and benefits can be observed for medium-chain fatty acids (neuroprotection/neurolepsis) and short-chain fatty acids (trophic effects on intestine). According to an exemplary aspect, provided are parenteral triglyceride oil-in-water emulsions containing selected long-chain and medium-chain fatty acids in specific concentrations as possible therapeutic agents in acute diseases. For example, the parenteral route has been chosen since the bioavailability of potentially therapeutic fatty acids is 100% for intravenous infusion, and consequently rapid incorporation into cell membranes (in 6-24 hours), compared to enteral infusion (in 4-5 days) and oral intake of soft gelatin capsules (in 8-10 weeks). In the acute care setting, rapid onset can be desirable, and thus, intravenous therapy is employed in an exemplary embodiment.

According to an exemplary aspect, a composition is provided comprising a triglyceride containing glycerol which is esterified with three FAs, wherein the three FAs are the same as each other, wherein three FAs of a selected pure triglyceride include at least one specific FA selected from the group consisting of caprylic acid, capric acid, α-linolenic acid, linoleic acid, oleic acid, arachidonic acid, eicosapentaenoic acid, docosahexaenoic acid and/or docosapentaenoic acid; and wherein the total amount of caprylic acid, capric acid, α-linolenic acid, linoleic acid, oleic acid, arachidonic acid, eicosapentaenoic acid, docosahexaenoic acid and docosapentaenoic acid in a pure triglyceride is ideally, at least greater than 60%, and preferably greater than 80%, based on the total weight of the FAs present.

According to another exemplary aspect, the composition contains a triglyceride in which two of the FAs are the same as each other, and the third FAs is different from the other two FAs, or the three FAs are different from each other.

According to another exemplary aspect, a concentrated triglyceride, suitable for intravenous administration, and comprising an amount of a pure or nearly pure single FA is prepared as a starting or stock lipid injectable emulsion, that can be used alone, or in combination with other similarly prepared pure or nearly pure FAs-triglyceride emulsions as physical mixtures.

According to another exemplary aspect, wherein stock lipid injectable emulsions containing a fixed oil concentration in water (e.g., preferably 20 g/100 mL) serve as building blocks to the formulator to enable the clinician to test and provide precise doses of therapeutically active FA(s) for a given clinical condition.

According to an exemplary aspect, a method of parenterally administering a composition to treat a predetermined condition is provided, the method comprising parenterally administering a composition comprising a triglyceride containing glycerol which is esterified with three FAs, to a person having the predetermined condition, wherein the three FAs do not include any FAs which do not contribute to treating the predetermined condition.

According to another exemplary aspect, the method employs a composition containing a triglyceride in which two of the FAs are the same as each other, and the third FA is different from the other two FAs, or the three FAs are different from each other, wherein the three FAs include at least one FA selected from the group consisting of caprylic acid, capric acid, α-linolenic acid, linoleic acid, oleic acid, arachidonic acid, eicosapentaenoic acid, docosahexaenoic acid and docosapentaenoic acid.

According to another exemplary aspect, multiple permutations containing various combinations and concentrations of selected FAs as physical mixtures are investigated for particular therapeutic benefits.

According to another exemplary aspect, said stock emulsions are directed to specific clinical conditions as therapeutic agents as a single FA-containing emulsion, or a combination containing multiple single FA-containing emulsions as physical mixtures from multiple emulsions.

According to another exemplary aspect, for each clinical condition investigated, a specific FA concentration, and/or combination thereof as physical mixtures, is identified as the final composition and contains at least 12 g, and preferably 16 g or greater of selected FAs per 100 mL of a triglyceride oil-in-water injectable emulsion, based on an optimal therapeutic response.

According to another exemplary aspect, once a final composition of fatty acid(s) has been optimized to a desirable therapeutic outcome, the final formulation can be made that combines the necessary triglyceride oils during manufacture to yield a single oil-in-water emulsion.

According to an exemplary aspect, the total amount of caprylic acid, capric acid, α-linolenic acid, linoleic acid, oleic acid, arachidonic acid, eicosapentaenoic acid, docosahexaenoic acid and docosapentaenoic acid is greater than 60%, for example, greater than 75%, for example, 80% or greater, for example, 85% or greater, for example, 95% or greater, for example, 99% or greater, based on the total weight of the FAs in the composition.

According to an exemplary aspect, a content of the FAs present in the at least one triglyceride containing glycerol which is esterified with three FAs that are the same as each other, is greater than 60%, for example, greater than 75%, for example, 80% or greater, for example, 85% or greater, for example, 95% or greater, for example, 99% or greater, based on the total weight of the FAs in the composition. For example, the composition can be substantially free of a triglyceride formed from two different FAs. In an exemplary embodiment, substantially all of the triglycerides of the composition are formed from the same FA.

According to an exemplary aspect, the composition, or each separately contained composition of a system, is a triglyceride-based oil-in-water emulsion, wherein the oil concentration is 10-30%$_{w/v}$ in water, for example, 15-25%$_{w/v}$ in water, for example, 20%$_{w/v}$ in water.

According to an exemplary aspect, a composition is provided containing at least two different triglycerides each having three FAs that are the same as each other. For example, the first triglyceride can be formed from a particular FA, for example, described herein, and the second triglyceride can be formed from a different FA, for example, described herein.

According to an exemplary aspect, a system for formulating a composition for parenteral administration is provided, the system comprising:

a first composition containing at least one triglyceride containing a glycerol which is esterified with three FAs, wherein the three FAs are caprylic acid, wherein a content of the caprylic acid present in the at least one triglyceride is greater than 60%, based on a total weight of FAs of the first composition;

a second composition containing at least one triglyceride containing a glycerol which is esterified with three FAs, wherein the three FAs are capric acid, wherein a content of the capric acid present in the at least one triglyceride is greater than 60%, based on a total weight of FAs of the second composition;

a third composition containing at least one triglyceride containing a glycerol which is esterified with three FAs, wherein the three FAs are α-linolenic acid, wherein a content of the α-linolenic acid present in the at least one triglyceride is greater than 60%, based on a total weight of fatty acids of the third composition;

a fourth composition containing at least one triglyceride containing a glycerol which is esterified with three FAs, wherein the three FAs are linoleic acid, wherein a content of the linoleic acid present in the at least one triglyceride is greater than 60%, based on a total weight of FAs of the fourth composition;

a fifth composition containing at least one triglyceride containing a glycerol which is esterified with three FAs, wherein the three FAs are oleic acid, wherein a content of the oleic acid present in the at least one triglyceride is greater than 60%, based on a total weight of FAs of the fifth composition;

a sixth composition containing at least one triglyceride containing a glycerol which is esterified with three FAs, wherein the three FAs are arachidonic acid, wherein a content of the arachidonic acid present in the at least one triglyceride is greater than 60%, based on a total weight of FAs of the sixth composition;

a seventh composition containing at least one triglyceride containing a glycerol which is esterified with three FAs, wherein the three FAs are eicosapentaenoic acid, wherein a content of the eicosapentaenoic acid present in the at least one triglyceride is greater than 60%, based on a total weight of FAs of the seventh composition;

an eighth composition containing at least one triglyceride containing a glycerol which is esterified with three FAs, wherein the three fatty acids are docosahexaenoic acid, wherein a content of the docosahexaenoic acid present in the at least one triglyceride is greater than 60%, based on a total weight of FAs of the eighth composition;

a ninth composition containing at least one triglyceride containing a glycerol which is esterified with three FAs, wherein the three FAs are docosapentaenoic acid, wherein a content of the docosapentaenoic acid present in the at least one triglyceride is greater than 60%, based on a total weight of FAs of the ninth composition, wherein each of the compositions is separately contained from each other.

According to an exemplary aspect, a system for formulating a composition for parenteral administration is provided, including at least two separately contained compositions, for example, at least five separately contained compositions, and for example, nine or less separately contained compositions.

According to an exemplary aspect, provided is a method of producing the desired composition, the method comprising: providing a triglyceride containing glycerol which is esterified with three FAs, wherein the total amount of caprylic acid, capric acid, α-linolenic acid, linoleic acid, oleic acid, arachidonic acid, eicosapentaenoic acid, docosahexaenoic acid and docosapentaenoic acid is not less than 60%, based on the total weight of the FAs; and modifying the structure of the triglycerides such that the total amount of caprylic acid, capric acid, α-linolenic acid, linoleic acid, oleic acid, arachidonic acid, eicosapentaenoic acid, docosahexaenoic acid and docosapentaenoic acid of the triglyceride is not less than 60%, based on the total weight of the FAs.

Disclosed are therapeutic indications of highly purified and highly concentrated FAs (Table 1) in parenteral dosage forms for treatment of several clinical conditions. According to an exemplary aspect, a method of parenterally administering a unique composition is provided, the method comprising parenterally administering to a person a composition containing a triglyceride oil consisting of the n3-long chain FAs, e.g., alpha-linolenic acid (ALA), eicosapentaenoic acid (EPA), docosahexaenoic acid (DHA), and docosapentaenoic acid (DPA) and/or consisting of the n-6 long chain FAs, e.g., linoleic acid, arachidonic acid (AA), and/or consisting of the n-9 long chain FA, e.g., oleic acid (OA), and/or the medium-chain FAs, e.g., caprylic acid and capric acid, in a parenteral oil-in-water emulsion as an alternative and exemplary composition of purified FAs compared to unpurified, natural sources. Plant and marine lipid mixtures for parenteral infusion can deliver at least between 12 to 16 g of various FAs per 100 mL of triglyceride. For example, in soybean oil triglycerides, approximately 85% of the FAs profile is comprised of LA, OA and ALA. In contrast, the customized formulations described herein, when expressed as triglycerides, would ideally contain only a selected FA or a predefined group of therapeutic FAs in specific concentrations depending upon the treatment indication(s).

An exemplary embodiment is first directed to producing a series of uniquely-prepared base or stock compositions comprising a purified triglyceride mostly containing a single selected FA esterified to all 3 positions on the glycerol molecule (Table 2). Moreover, these exemplary "starting" formulations can at least contain 60%, and ideally contain >80% of the specified FA and minimal to no unintended, unnecessary or undesirable FAs.

Another exemplary embodiment is directed to the type and concentration of lipids in the base or stock emulsion compositions, wherein the composition is a triglyceride-based oil-in-water emulsion, wherein the oil concentration is ideally 20%$_{w/v}$ in water, wherein the emulsions contain desirable excipient(s) suitable for intravenous administration, wherein the emulsions manufactured are sterilized and sufficiently stable for intravenous administration.

Another exemplary embodiment is directed to a method of parenterally administering a composition, the method comprising: parenterally administering to a person a composition containing an omega-3 FA(s) and/or an omega-6 FA(s) and/or an omega-9 FA and/or a medium chain FA(s), in a parenteral oil-in-water emulsion, as an alternative method of delivery of a therapeutic FA from a purified triglyceride composition or a combination of therapeutic FAs from a mixture of purified triglyceride compositions, compared to unpurified sources of FAs.

In another exemplary embodiment, a method of preparation comprising:
wherein the omega-3 FAs comprises eicosapentaenoic acid (EPA), docosahexaenoic acid (DHA), docosapentaenoic acid (DPA) or alpha linolenic acid (ALA) or a mixture thereof, wherein, the omega-6 FAs comprises arachidonic acid (AA) or linoleic acid or a mixture thereof, wherein the omega-9 FA comprises oleic acid, wherein the medium chain FAs comprises caprylic acid or capric acid or a mixture thereof.

In another exemplary embodiment, a method of parenterally administering a composition is provided, the method comprising parenterally administering to a person a composition containing selected amounts of therapeutic FAs as a physical mixture of oil triglycerides (TGs) in a parenteral oil-in-water emulsion. An exemplary aspect is to create a dosage form suitable for testing a broad therapeutic dose range of FA(s) in selected diseases, to ascertain a dose-response, such as application of a fractional factorial design.

For example, standard 20% w/v oil-in-water injectable emulsions made as purified products, primarily containing a single FA attached to triglyceride molecules, are shown in Table 3. A final emulsion containing a selected FA or a mixture for a particular therapeutic indication can be identified. Examples of such emulsion physical mixtures are shown in Tables 4 and 5. These formulations may also be constructed by combining the oils into a single physical mixture in the desired proportions, and made as single emulsion. The final formulation would include a highly purified injectable emulsion primarily, if not exclusively, containing only specific FAs in selected therapeutic concentrations covering a broad range of FAs as shown in Table 6.

This approach greatly contrasts with current lipid injectable emulsion formulations made from plant or marine oil triglycerides, largely used for nutritional purposes. For example, fish oil triglycerides can provide approximately between 30 and 60% of the fatty acid profile as omega-3 FAs in accordance with currently-approved monographs in the European Pharmacopeia. The remaining FAs include other saturated and unsaturated FAs that have little or no additional therapeutic effect, and in some cases, may even produce undesirable or adverse metabolic effects, especially during critical illness. Such a source, as defined in this application, would be highly purified, containing little or no other FAs than those intended.

In another exemplary embodiment, it may even be desirable to produce an oil-in-water injectable emulsion that contains EPA and DHA, along with other FAs for specific metabolic indications. For example, medium-chain FAs (8 to 10 carbons) such as caprylic and capric acids, respectively, may be included to augment the neuroprotective effects of n3-FAs in the treatment of chronic neurological diseases or acute therapy for traumatic brain injury. In other clinical conditions, there may be a need to include arachidonic acid to prevent complications from essential fatty acid deficiency (EFAD) in chronic conditions such as long-term total parenteral nutrition therapy, or for acute therapy in premature infants, to prevent or mitigate retinopathy of prematurity (ROP). These additional fatty acids could be provided in the oil phase as physical mixtures of triglycerides as oil-in-water injectable emulsions. Exemplary examples of possible parenteral emulsion compositions employing therapeutic combinations of fatty acids are shown in Tables 4, 5, 6 and 7.

In another exemplary embodiment, the method of determining the final therapeutic formulation can include, for example, six stages of development:
STAGE-1: Identify potentially therapeutic Fas;
STAGE-2: Make pure triglycerides that mainly contain a single potentially therapeutic, FA;
STAGE-3: Produce a stock or starting oil-in-water emulsion for each purified triglyceride;
STAGE-4: Connect a FA or combination of FAs that may have therapeutic benefit in a selected disease;
STAGE-5: Construct broad ranges of FA concentrations to investigate potential therapeutic benefits by mixing various volume ratios of starting emulsions;
STAGE-6: Manufacture the final, optimized FA-containing mixture as a single oil-in-water emulsion for each disease.

In another exemplary embodiment, a method of parenterally administering a composition is provided, the method comprising parenterally administering to a person a composition containing specific concentrations of therapeutic FAs in a purified parenteral oil-in-water emulsion that, when given intravenously, will result in improved plasma clearance over triglyceride-based injectable emulsions. Using highly purified combinations of selected therapeutic FAs avoids the presence of undesirable long-chain FAs that may alter uptake into target tissues. Improvements in plasma clearance of lipids, and the avoidance of, for example, hypertriglyceridemia, is a desirable goal in acutely ill patients, especially those with pre-existing lipid disorders or in critically ill infants. For example, triglyceride-based injectable emulsions can cause hypertriglyceridemia, based on oil composition (e.g., soybean oil triglycerides), infusion rate (e.g., long-chain triglycerides>0.11 g/kg/hour), phospholipid-to-triglyceride concentration (PL:TG ratio>0.06), and the patient's predisposition to lipid intolerance (age, genetics, and/or that induced by disease(s) and/or drug(s)).

In another exemplary embodiment, a method of parenterally administering a composition is provided, the method comprising parenterally administering to a person a composition of specific concentrations of therapeutic FAs in a purified parenteral oil-in-water emulsion that, when given Intravenously, will result in rapid incorporation into plasma cell membranes and provide acute treatment (prevention and/or mitigation) of several clinical conditions. This is largely a function of the route of administration, wherein intravenous administration is 100% bioavailable. This is in contrast to other typical routes of administration (e.g., subcutaneous, enteral, topical), where barriers to absorption exist that vastly reduce bioavailability, which includes delayed onset of desirable therapeutic effects. This fact is most evident during clinical investigations of omega-3 FAs therapy where the time to achieve therapeutic benefits varies from 8-10 weeks (via oral capsules) to 4-5 days (via continuous enteral delivery from a feeding tube) to 6-24 hours (via continuous intravenous infusion). Rapid incorporation into membranes is an especially important aspect of its efficacy in this application from two perspectives. First, for example, the composition of cell membranes in the critically ill patient is determined from recent dietary intakes, and in the western world, for example, would be expected to be largely comprised of omega-6 FAs. Thus, such patients have a heightened pro-inflammatory response that aggravates the underlying disease(s) present. Second, as a result of the current omega-6-rich milieu, rapidly changing the composition to a less inflammatory or anti-inflammatory state is desirable, and providing a dosage form containing very high concentrations of omega-3 FAs that are readily incorporated into cells and metabolized could reduce the injurious effects on vital organ functions and resulting adverse outcomes.

The following clinical conditions are examples of acute metabolic stress that accompanies critical illness or presents as a life-threatening situation which may be treatable by specially designed, highly purified mixtures of selected FAs:
1. Systemic Inflammatory Response Syndrome (SIRS)
2. Severe Hypertriglyceridemia
3. Severe Hepatic Steatosis
4. Retinopathy of Prematurity (ROP)
5. Acute Tubular Necrosis (ATN)
6. IgA Nephropathies
7. Ischemia-Reperfusion Injury
8. Traumatic Brain Injury (TBI)
9. Multi-system Organ Failure (MOF)
10. Respiratory Distress Syndrome (RDS)
11. Acute Myocardial Infarction (MI)
12. Status Anginosus
13. Status Asthmaticus
14. Status Epilepticus
15. Status Lacunaris
16. Inflammatory Bowel Disease (regional enteritis, ulcerative colitis)
17. Severe (debilitating) Arthritis
18. Severe Psoriasis
19. $3^{rd}$ Degree Burns
20. Acute Pancreatitis Exemplary injectable emulsion compositions described herein are therefore, for example, designed to maximize the concentrations of selected FAs for therapeutic purposes from various physical and/or structured emulsion mixtures. Exemplary injectable emulsions are also designed to minimize the infusion of unnecessary and/or undesirable FAs. Current lipid injectable emulsions are made from plant or marine oil triglycerides, and thus contain numerous FAs and concentrations depending on the source(s). As well, neither do the structured triglycerides (Tables 8 and 9) offer the dosing precision that would be achievable in this application. Therefore, these specially designed injectable emulsions, as physical mixtures, can provide more precise amounts of various FAs and reduce or eliminate the presence of undesirable and/or extraneous FAs and therefore they may favorably modulate and/or treat various diseases.

The emulsions and examples presented in the application are not meant to be limiting in any way. The emulsion compositions provided as examples illustrate the flexibility and precision to maximize the investigation into selected FAs as potential pharmacological agents. Similarly, the clinical examples are only intended to illustrate some of the clinical conditions encountered in the ICU or under life-threatening conditions where the acute treatment via parenteral infusion of certain FAs and/or combinations thereof, may have rapid therapeutic benefits. For example, those skilled in the art of critical care and emergency medicine could certainly prescribe FAs therapy as described herein, or in any clinical circumstance where clinical manifestations of disease involving inflammation, oxidative stress, ischemia and/or immune dysfunction have pathological implications in acutely ill medical or surgical patients. As well, those skilled in the art of chronic inflammatory diseases or neurological conditions could similarly prescribe exemplary FAs therapy during acute exacerbations of the disease. Thus, exemplary lipid injectable emulsion formulations, as described in this application, offer a unique opportunity to target certain diseases with potentially therapeutic FAs in a stable emulsion, and in precise dosages that minimize the potentially negative impact of unnecessary or undesirable FAs normally found in triglyceride oils of plant or marine origin.

According to an exemplary aspect, a method of parenterally administering a composition is provided, the method comprising parenterally administering to a person a composition containing selected amounts of therapeutic FAs as a structured mixture of oil TGs in a parenteral oil-in-water emulsion.

According to an exemplary aspect, a method of parenterally administering a composition is provided, the method comprising parenterally administering to a person a composition containing selected amounts of therapeutic FAs as a physical mixture of oils containing triglycerides (TGs), and optionally ethyl esters (EEs), in a parenteral oil-in-water emulsion.

According to an exemplary aspect, a method of parenterally administering a composition is provided, the method comprising parenterally administering to a person a composition containing selected amounts of therapeutic FAs as a structured mixture of oils containing TGs and EEs in a parenteral oil-in-water emulsion.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat systemic inflammatory response syndrome (SIRS).

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat severe hypertriglyceridemia.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat severe hepatic steatosis.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat retinopathy of prematurity (ROP).

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat acute tubular necrosis (ATN).

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat IgA nephropathies.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat ischemia-reperfusion injury.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat traumatic brain injury (TBI).

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat multiple organ failure syndrome (MOFS).

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat adult or infant respiratory syndrome (RDS).

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat acute myocardial infarction (MI).

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat status anginosis.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat status asthmaticus.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat status epilepticus.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat status lacuranis.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat inflammatory bowel disease.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat debilitating arthritis.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat severe psoriasis.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat $3^{rd}$ degree burns.

According to an exemplary aspect, a method of parenterally administering a composition is provided, the method comprising parenterally administering to a person a composition containing EPA and/or DHA and/or DPA and/or ALA and/or AA and/or LA and/or OA and/or caprylic acid and/or capric acid to selectively treat acute pancreatitis.

Examples

TABLE 1

Selected Fatty Acids for Therapeutic Purposes

| Selected Fatty Acid | Chemical Notation | Molecular Formula | Molecular Weight |
|---|---|---|---|
| caprylic acid | 8:0 | $C_8H_{16}O_2$ | 144 |
| capric acid | 10:0 | $C_{10}H_{20}O_2$ | 172 |
| α-linolenic acid | 18:2n3 | $C_{18}H_{30}O_2$ | 278 |
| linoleic acid | 18:2n6 | $C_{18}H_{32}O_2$ | 280 |
| oleic acid | 18:1n9 | $C_{18}H_{34}O_2$ | 283 |
| arachidonic acid | 20:4n6 | $C_{20}H_{32}O_2$ | 305 |
| eicosapentaenoic acid | 20:5n3 | $C_{20}H_{30}O_2$ | 303 |
| docosahexaenoic acid | 22:6n3 | $C_{22}H_{32}O_2$ | 328 |
| docosapentaenoic acid | 22:5n3 | $C_{22}H_{34}O_2$ | 331 |

TABLE 2

Sample of Purified Fatty Acid Triglycerides (F.A.T.) for Physical Mixtures
Physical Mixtures (Blended Triglycerides)

| | | | | |
|---|---|---|---|---|
| ⊢$C_8$ | ⊢$C_{10}$ | ⊢$C_{18}$ | ⊢$C_{20}$ | ⊢$C_{22}$ |
| ⊢$C_8$ + | ⊢$C_{10}$ + | ⊢$C_{18}$ + | ⊢$C_{20}$ + | ⊢$C_{22}$ |
| ⊢$C_8$ | ⊢$C_{10}$ | ⊢$C_{18}$ | ⊢$C_{20}$ | ⊢$C_{22}$ |

TABLE 3

Sample of Purified Fatty Acid Triglycerides (F.A.T.) as Physical Emulsion Mixtures from Purified 20%$_{w/v}$ Stock Oil-in-Water Emulsions

| 20%$_{w/v}$ Emulsion with Single F.A.T.* | ~M.W. of Triglyceride | Concentration Range in Mixture, g (as TGs) | Concentration Range in Mixture, mL |
|---|---|---|---|
| [a]Caprylic | 470 g | 0-162 | 0-1000 |
| [b]Capric | 554 g | 0-166 | 0-1000 |
| [c]α-Linolenic | 872 g | 0-178 | 0-1000 |
| [d]Linoleic | 878 g | 0-178 | 0-1000 |
| [e]Oleic | 887 g | 0-178 | 0-1000 |
| [f]Arachidonic | 953 g | 0-180 | 0-1000 |
| [g]Eicosapentaenoic | 947 g | 0-180 | 0-1000 |
| [h]Docosapentaenoic | 1022 g | 0-182 | 0-1000 |
| [i]Docosahexaenoic | 1031 g | 0-182 | 0-1000 |

*Expressed as triglycerides (TG).
[a]Assumes ~81% of pure TG emulsion is Caprylic Acid
[b]Assumes ~83% of pure TG emulsion is Capric Acid
[c]Assumes ~89% of pure TG emulsion is α-Linolenic Acid
[d]Assumes ~89% of pure TG emulsion is Linoleic Acid
[e]Assumes ~89% of pure TG emulsion is Oleic Acid
[f]Assumes ~90% of pure TG emulsion is Arachidonic Acid
[g]Assumes ~90% of pure TG emulsion is Eicosapentaenoic Acid
[h]Assumes ~91% of pure TG emulsion is Docosapentaenoic Acid
[i]Assumes ~91% of pure TG emulsion is Docosahexaenoic Acid

TABLE 4

Sample Formulations of Purified Fatty Acid Triglycerides (F.A.T.) as Physical Emulsion Mixtures from Purified 20% w/v Stock Oil-in-Water Emulsions

| | 20%$_{w/v}$ Emulsion Containing a Single F.A.T.* Volume of Each Emulsion in Sample Formulations | | | | | | | | |
|---|---|---|---|---|---|---|---|---|---|
| FORMULATION# | 1 | 2 | 3 | 4 | 5 | 6 | 7 | 8 | 9 |
| [a]Caprylic | 7.50 | 22.50 | 37.50 | 7.50 | 22.50 | 37.50 | 7.50 | 22.50 | 37.50 |
| [b]Capric | 2.50 | 7.50 | 12.50 | 2.50 | 7.50 | 12.50 | 2.50 | 7.50 | 12.50 |
| [c]α-Linolenic | 3.0 | 3.0 | 3.0 | — | — | — | 0.11 | — | — |
| [d]Linoleic | 3.0 | 3.0 | 3.0 | — | — | — | 0.53 | — | — |
| [e]Oleic | 6.0 | 6.0 | 6.0 | — | — | — | 0.26 | 0.45 | — |
| [f]Arachidonic | 0.45 | 0.45 | 0.45 | 0.90 | 0.90 | 0.90 | — | 0.45 | 0.45 |
| [g]Eicosapentaenoic | 40.33 | 14.11 | 17.47 | 32.04 | 35.90 | 23.09 | 46.06 | 33.08 | 20.09 |
| [h]Docosapentaenoic | — | — | — | — | — | — | — | — | 0.45 |
| [i]Docosahexaenoic | 36.22 | 41.44 | 17.08 | 53.06 | 28.02 | 20.01 | 36.04 | 28.02 | 20.01 |
| FINAL VOLUME, mLs | 100 | 100 | 100 | 100 | 100 | 100 | 100 | 100 | 100 |

*Expressed as triglycerides (TG).
[a]Assumes ~81% of pure TG emulsion is Caprylic Acid
[b]Assumes ~83% of pure TG emulsion is Capric Acid
[c]Assumes ~89% of pure TG emulsion is α-Linolenic Acid
[d]Assumes ~89% of pure TG emulsion is Linoleic Acid
[e]Assumes ~89% of pure TG emulsion is Oleic Acid
[f]Assumes ~90% of pure TG emulsion is Arachidonic Acid
[g]Assumes ~90% of pure TG emulsion is Eicosapentaenoic Acid
[h]Assumes ~91% of pure TG emulsion is Docosapentaenoic Acid
[i]Assumes ~91% of pure TG emulsion is Docosahexaenoic Acid

TABLE 5

Sample Formulations of Purified Fatty Acid Triglycerides (F.A.T.) as Physical Emulsion Mixtures from Purified 20% w/v Stock Oil-in-Water Emulsions Single F.A.T.*
Grams of Bioactive Fatty Acids in Each Emulsion in Sample Formulations

| FORMULATION# | 1 | 2 | 3 | 4 | 5 | 6 | 7 | 8 | 9 |
|---|---|---|---|---|---|---|---|---|---|
| [a]Caprylic | 1.215 | 3.645 | 6.075 | 1.215 | 3.645 | 6.075 | 1.215 | 3.645 | 6.075 |
| [b]Capric | 0.415 | 1.125 | 2.075 | 0.415 | 1.125 | 2.075 | 0.415 | 1.125 | 2.075 |
| [c]α-Linolenic | 0.534 | 0.534 | 0.534 | — | — | — | 0.019 | — | — |
| [d]Linoleic | 0.534 | 0.534 | 0.534 | — | — | — | 0.094 | — | — |
| [e]Oleic | 1.068 | 1.068 | 1.068 | — | — | — | 0.046 | 0.081 | — |
| [f]Arachidonic | 0.081 | 0.081 | 0.081 | 0.162 | 0.162 | 0.162 | — | 0.081 | 0.081 |
| [g]Eicosapentaenoic | 7.259 | 2.539 | 3.684 | 6.487 | 7.362 | 5.236 | 9.550 | 7.394 | 5.236 |
| [h]Docosapentaenoic | — | — | — | — | — | — | — | — | 0.081 |
| [i]Docosahexaenoic | 6.774 | 7.906 | 3.108 | 9.656 | 5.132 | 3.641 | 6.559 | 5.099 | 3.641 |
| TOTAL Fatty Acids, g/100 mLs | 17.88 | 17.55 | 17.15 | 17.93 | 17.54 | 17.18 | 17.89 | 17.54 | 17.18 |

*Expressed as triglycerides (TG).
[a]Assumes ~81% of pure TG emulsion is Caprylic Acid
[b]Assumes ~83% of pure TG emulsion is Capric Acid
[c]Assumes ~89% of pure TG emulsion is α-Linolenic Acid
[d]Assumes ~89% of pure TG emulsion is Linoleic Acid
[e]Assumes ~89% of pure TG emulsion is Oleic Acid
[f]Assumes ~90% of pure TG emulsion is Arachidonic Acid
[g]Assumes ~90% of pure TG emulsion is Eicosapentaenoic Acid
[h]Assumes ~91% of pure TG emulsion is Docosapentaenoic Acid
[i]Assumes ~91% of pure TG emulsion is Docosahexaenoic Acid

TABLE 6

Sample % Fatty Acid Compositions By Chain Length

| ≥20 Carbons | |
|---|---|
| Arachidonic Acid (AA) | 0-5% |
| Eicosapentaenoic Acid (EPA) | 0-90% |
| Docosahexaenoic Acid (DHA) | 0-90% |
| 18 Carbons | |
| Linoleic Acid (LA) | 0-50% |
| Alpha Linolenic Acid (ALA) | 0-10% |
| Oleic Acid (OA) | 0-65% |
| 8-10 Carbons | |
| Caprylic Acid | 0-75% |
| Capric Acid | 0-20% |

TABLE 7

Sample Injectable Emulsion Compositions

| Pharmaceutical Ingredient | Range of Concentrations, g/mL |
|---|---|
| Sample No. 1 | See Table 3 |
| Sample No. 2 | See Table 3 |
| Sample No. 3 | See Table 3 |
| Sample No. 4 | See Table 3 |
| Sample No. 5 | See Table 3 |
| Sample No. 6 | See Table 3 |
| Sample No. 7 | See Table 3 |
| Sample No. 8 | See Table 3 |
| Glycerol | 0.02 to 0.04 |
| Phospholipids | 0.01 to 0.04 |
| Sodium Oleate | 0.00 to 0.005 |
| α-tocopherol | 0.00 to 0.002 |
| Sodium Hydroxide | qs ad |
| Water for Injection | qs ad |
| Other Excipients* | qs ad |

*Additional pharmaceutical excipients may be used to stabilize the formulation and make it suitable for intravenous administration.

TABLE 8

Sample of Purified Fatty Acid triglycerides (F.A.T.) as Structured Emulsions

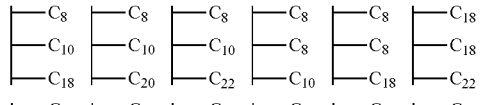
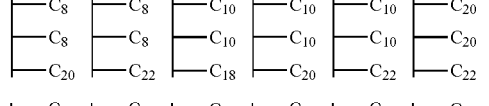
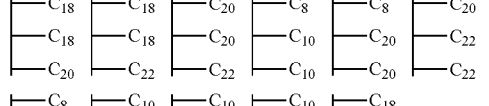
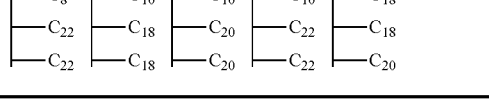

TABLE 9

Sample of Purified Fatty Acid Triglycerides (F.A.T.) as Structured Emulsion Mixtures

| | | | | |
|---|---|---|---|---|
| ⎡─$C_8$<br>⎢─$C_{10}$ +<br>⎣─$C_{20}$ | ⎡─$C_8$<br>⎢─$C_{10}$<br>⎣─$C_{22}$ | | | |
| ⎡─$C_8$<br>⎢─$C_{10}$ +<br>⎣─$C_{20}$ | ⎡─$C_8$<br>⎢─$C_{10}$ +<br>⎣─$C_{22}$ | ⎡─$C_8$<br>⎢─$C_{20}$<br>⎣─$C_{22}$ | | |
| ⎡─$C_8$<br>⎢─$C_{10}$ +<br>⎣─$C_{20}$ | ⎡─$C_8$<br>⎢─$C_{10}$ +<br>⎣─$C_{22}$ | ⎡─$C_8$<br>⎢─$C_{20}$ +<br>⎣─$C_{20}$ | ⎡─$C_8$<br>⎢─$C_{22}$<br>⎣─$C_{22}$ | |
| ⎡─$C_8$<br>⎢─$C_{10}$ +<br>⎣─$C_{20}$ | ⎡─$C_8$<br>⎢─$C_{18}$ +<br>⎣─$C_{20}$ | ⎡─$C_8$<br>⎢─$C_{18}$ +<br>⎣─$C_{22}$ | ⎡─$C_{20}$<br>⎢─$C_{20}$ +<br>⎣─$C_{22}$ | ⎡─$C_{20}$<br>⎢─$C_{22}$<br>⎣─$C_{22}$ |

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

REFERENCES

Bach A C, Frey A, Lutz O. Clinical and experimental effects of medium-chain-triglyceride-based fat emulsions—A review. Clin Nutr 1989; 8:223-35.

Calder P C. The 2008 ESPEN Sir David Cuthbertson lecture: Fatty acids and inflammation—From the membrane to the nucleus and from the laboratory bench to the clinic. Clin Nutr 2010; 29:5-12.

Driscoll D F, McMahon M M, Blackburn G L et al. Phenytoin toxicity in a critically ill, hypoalbuminemic patient with normal serum drug concentrations. Crit Care Med 1988; 16:1248-1249.

Driscoll D F, Nehne J, Franke R et al. The stabilizing influence of medium-chain triglycerides on the stability of all-in-one formulations. Int J Pharm 2002:240:1-10.

Driscoll D F. Lipid injectable emulsions: Pharmacopeial and safety issues. Pharm Res 2006; 23:1959-69.

Driscoll D F, Bistrian B R. Parenteral and enteral nutrition in the intensive care unit. Intensive Care medicine, Irwin R S, Rippe J M (eds.) Wolters Kluwer| Lippincott Williams Wilkins, Philadelphia, 2012, pp. 1974-90.

Driscoll D F, Ling P R, Bistrian B R. Pharmacopeial compliance of fish oil-containing parenteral lipid emulsion mixtures: Globule size distribution (GSD) and fatty acid analyses. Int J. Pharm. 2009; 379(1):125-30.

Fish oil, rich in omega-3 fatty acid. 2008, Monograph No. 1912, European Pharmacopeia, 6.0, pp 1893-95.

Harris W S. The omega-3 index: Clinical utility for therapeutic intervention. Curr cardiol Rep 2010; 12:503-08.

Lee J S, Pinnamaneni S K, Eo S J et al. Saturated, but not n6 polyunsaturated, fatty acids induce insulin resistance: role of accumulation of lipid metabolites. J Appl Physiol 2006; 100:1467-74.

Lovaza™ (omega-3 acid ethyl esters) Capsules. Package insert. Reliant Pharmaceuticals, Inc., Liberty Corner, N.J., USA, June 2007.

Lowell J A, Schifferdecker C, Driscoll D F et al. Postoperative fluid overload: Not a benign problem. Crit Care Med 1990; 18:728-733.

Maalouf M A, Rho J M, Mattson M R The neuroprotective properties of calorie restriction, the ketogenic diet, and ketone bodies. Brain Res Rev 2009; 59:293-315.

Omega-3 Acid Triglycerides, 2008. Monograph No. 1352. European Pharmacopeia, 6.3, pp 4246-4248.

Rangel-Fausto M S, Pittet D, Costigan M et al. The natural history of systemic inflammatory response syndrome (SIRS): A prospective study. JAMA 1995; 273:117-23.

Senior J R. Medium Chain Triglycerides. University of Pennsylvania Press, Philadelphia, 1968.

Serhan C N, Chiang N, Van Dyke T E. Resolving inflammation: dual anti-inflammatory and pro-resolution lipid mediators. Nature Review 2008; 8:349-61.

Simopoulos A. Evolutionary aspects of dietary omega-3 fatty acid ratio: Medical implications. World Rev Nutr Diet 2009; 100:1-21.

Wanten G J A, Calder P C. Immune modulation by parenteral lipid emulsions. Am J Clin Nutr 2007; 85:1171-84.

What is claimed is:

1. A composition comprising at least one triglyceride containing glycerol which is esterified with three fatty acids, wherein the three fatty acids are the same as each other, wherein each of the three fatty acids that are the same as each other is caprylic acid, capric acid, α-linolenic acid, linoleic acid, oleic acid, arachidonic acid, eicosapentaenoic acid, docosahexaenoic acid or docosapentaenoic acid, and wherein a total amount of caprylic acid, capric acid, α-linolenic acid, linoleic acid, oleic acid, arachidonic acid, eicosapentaenoic acid, docosahexaenoic acid and docosapentaenoic acid is 95% or greater based on the total weight of the fatty acids, wherein the at least one triglyceride containing glycerol which is esterified with three fatty acids includes:
  a first triglyceride containing a glycerol which is esterified with three fatty acids, wherein each of the three fatty acids is docosahexaenoic acid,
  a second triglyceride containing a glycerol which is esterified with three fatty acids, wherein each of the three fatty acids is eicosapentaenoic acid, wherein a content of the eicosapentaenoic acid is greater than 60%, based on a total weight of fatty acids of the composition,
  a third triglyceride containing a glycerol which is esterified with three fatty acids, wherein each of the three fatty acids is caprylic acid, and
  a fourth triglyceride containing a glycerol which is esterified with three fatty acids, wherein each of the three fatty acids is capric acid, wherein the composition is an oil-in-water emulsion wherein the oil concentration is 10-30% w/v in water, wherein a content of the caprylic acid is 1.215 to 6.075 g per 100 mL of the composition, and a content of the capric acid is 0.415 to 2.075 g per 100 mL of the composition.

2. A method of parenterally administering a composition to treat a predetermined condition, the method comprising:
  parenterally administering the composition of claim 1 to a person having the predetermined condition,
  wherein the predetermined condition is selected from the group consisting of systemic inflammatory response syndrome, severe hypertriglyceridemia, severe hepatic steatosis, retinopathy of prematurity, acute tubular necrosis, IgA Nephropathies, ischemia-reperfusion injury, traumatic brain injury, multi-system organ failure, respiratory distress syndrome, acute myocardial infarction, status anginosus, status asthmaticus, status epilepticus, status lacunaris, inflammatory bowel disease, severe arthritis, severe psoriasis, third degree burns, and acute pancreatitis.

3. The method according to claim 2, wherein the three fatty acids of the first or second triglyiceride that are the same as each other contribute to treating the predetermined condition.

4. The method according to claim 2, wherein the composition is substantially free of fatty acids that do not contribute to treating the predetermined condition.

5. A composition comprising at least one triglyceride containing glycerol which is esterified with three fatty acids, wherein the three fatty acids are the same as each other,
wherein each of the three fatty acids that are the same as each other is caprylic acid, capric acid, α-linolenic acid, linoleic acid, oleic acid, arachidonic acid, eicosapentaenoic acid, docosahexaenoic acid or docosapentaenoic acid, and
wherein a content of the fatty acids present in the at least one triglyceride containing glycerol which is esterified with three fatty acids that are the same as each other, is greater than 95%, based on a total weight of fatty acids of the composition,
wherein the at least one triglyceride containing glycerol which is esterified with three fatty acids includes:
a first triglyceride containing a glycerol which is esterified with three fatty acids, wherein each of the three fatty acids is docosahexaenoic acid,
a second triglyceride containing a glycerol which is esterified with three fatty acids, wherein each of the three fatty acids is eicosapentaenoic acid, wherein a content of the eicosapentaenoic acid is greater than 60%, based on a total weight of fatty acids of the composition,
a third triglyceride containing a glycerol which is esterified with three fatty acids, wherein each of the three fatty acids is caprylic acid, and
a fourth triglyceride containing a glycerol which is esterified with three fatty acids, wherein each of the three fatty acids is capric acid,
wherein the composition is an oil-in-water emulsion wherein the oil concentration is 10-30% w/v in water,
wherein a content of the caprylic acid is 1.215 to 6.075 g per 100 mL of the composition, and a content of the capric acid is 0.415 to 2.075 g per 100 mL of the composition.

6. The composition of claim 5, wherein the composition con essentially of triglycerides each containing glycerol which is esterified with three fatty acids that are the same as each other.

7. A method of parenterally administering a composition to treat a predetermined condition, the method comprising:
parenterally administering the composition of claim 5 to a person having the predetermined condition,
wherein the predetermined condition is selected from the group consisting of systemic inflammatory response syndrome, severe hypertriglyceridemia, severe hepatic steatosis, retinopathy of prematurity, acute tubular necrosis, IgA Nephropathies, ischemia-reperfusion injury, traumatic brain injury, multi-system organ failure, respiratory distress syndrome, acute myocardial infarction, status anginosus, status asthmaticus, status epilepticus, status lacunaris, inflammatory bowel disease, severe arthritis, severe psoriasis, third degree burns, and acute pancreatitis.

8. The method according to claim 7, wherein the three fatty acids of the first or second triglyiceride that are the same as each other contribute to treating the predetermined condition.

9. The method according to claim 7, wherein the composition is substantially fatty acids that do not contribute to treating the predetermined condition.

10. A system for formulating a composition for parenteral administration, the system comprising at least a first composition and a second composition, wherein the first and second compositions are separately contained from each other, wherein the first composition is the composition according to claim 1, wherein the second composition contains at least one triglyceride containing a glycerol which is esterified with three fatty acids that are the same as each other, wherein a content of the fatty acids present in the at least one triglyceride is greater than 60%, based on a total weight of fatty acids of the first composition.

11. The system of claim 10, wherein the system comprises at least five separately contained compositions, wherein each composition contains at least one triglyceride containing a glycerol which is esterified with three fatty acids that are the same as each other, wherein a content of the fatty acids present in the at least one triglyceride is greater than 60%, based on a total weight of fatty acids of the first composition.

12. The system of claim 10, wherein each of the separately contained compositions is in a form of an emulsion.

13. A method of formulating a composition, the method comprising:
providing the system of claim 10; and
fixing at least two of the separately contained compositions.

14. A method of determining an effective formulation for treating a predetermined condition, the method comprising:
providing the system of claim 10;
mixing at least two of the separately contained compositions to produce a plurality of distinct samples; and
testing at least one of the distinct samples to determine whether the tested distinct sample is effective to treat the predetermined condition,
wherein the predetermined condition is selected from the group consisting of systemic inflammatory response syndrome, severe hypertriglyceridemia, severe hepatic steatosis, retinopathy of prematurity, acute tubular necrosis, IgA Nephropathies, ischemia-reperfusion injury, traumatic brain injury, multi-system organ failure, respiratory distress syndrome, acute myocardial infarction, status anginosus, status asthmaticus, status epilepticus, status lacunaris, inflammatory bowel disease, severe arthritis, severe psoriasis, third degree burns, and acute pancreatitis.

15. The composition of claim 1, wherein the composition is substantially free of a triglyceride formed from two different fatty acids.

16. A method of parenterally administering a composition, the method comprising parenterally administering the composition of claim 1 to a person.

17. A method of parenterally administering a composition, the method comprising parenterally administering the composition of claim 5 to a person.

* * * * *

UNITED STATES PATENT AND TRADEMARK OFFICE
CERTIFICATE OF CORRECTION

PATENT NO. : 9,861,605 B2
APPLICATION NO. : 14/354010
DATED : January 9, 2018
INVENTOR(S) : David F. Driscoll It is certified that error appears in the above-identified patent and that said Letters Patent is hereby corrected as shown below:

In the Specification

At Column 4, Line 30, after "18 carbons and", "2 double bonds" should read --3 double bonds--.

At Column 4, Line 32, after "denoted as", "18:2n3" should read --18:3n3--.

Signed and Sealed this
Third Day of July, 2018

Andrei Iancu
*Director of the United States Patent and Trademark Office*